United States Patent [19]

Masters et al.

[11] Patent Number: 5,855,871
[45] Date of Patent: Jan. 5, 1999

[54] EFFERVESCENT TWO COMPONENT BICARBONATE AND ACID CONTAINING DENTIFRICE

[75] Inventors: James Masters, Flemington; Kim Cervino, Somerset; David Viscio, Monmouth Junction; James Kemp, Somerset; Salim Nathoo, Piscataway, all of N.J.

[73] Assignee: Colgate-Palmolive Company, New York, N.Y.

[21] Appl. No.: 909,582

[22] Filed: Aug. 12, 1997

[51] Int. Cl.⁶ .............................. A61K 7/16; A61K 7/20; A61K 33/10
[52] U.S. Cl. .............................. 424/49; 424/44; 424/53; 424/57
[58] Field of Search ........................... 424/49–58

[56] References Cited

U.S. PATENT DOCUMENTS

| | | | |
|---|---|---|---|
| Re. 14,961 | 10/1920 | Rhein | 424/44 |
| 1,297,494 | 3/1919 | Rhein | 424/44 |
| 1,535,529 | 4/1925 | Hopkins | 424/44 |
| 4,098,435 | 7/1978 | Weyn | 222/94 |
| 4,211,341 | 7/1980 | Weyn | 222/94 |
| 4,487,757 | 12/1984 | Kiozpeoplou | 424/49 |
| 4,687,663 | 8/1987 | Schaeffer | 424/52 |
| 4,818,518 | 4/1989 | Gioffre et al. | 424/44 |
| 5,215,740 | 6/1993 | Domke . | |
| 5,474,761 | 12/1995 | Liang . | |
| 5,565,190 | 10/1996 | Santalucia et al. | 424/53 |
| 5,599,525 | 2/1997 | Hsu et al. | 424/53 |
| 5,599,527 | 2/1997 | Hsu et al. | 424/53 |
| 5,614,174 | 3/1997 | Hsu et al. | 424/53 |
| 5,683,680 | 11/1997 | Santalucia et al. | 424/53 |
| 5,690,913 | 11/1997 | Hsu et al. | 424/53 |

FOREIGN PATENT DOCUMENTS

| | | |
|---|---|---|
| 1 209 319 | 10/1970 | United Kingdom . |
| WO/PCT92/07550 | 5/1992 | WIPO . |
| WO/PCT93/11733 | 6/1993 | WIPO . |
| WO/PCT95/02392 | 1/1995 | WIPO . |
| WO/PCT97/46462 | 12/1997 | WIPO . |

OTHER PUBLICATIONS

Rustogi et al, The Journal of Clinical Dentistry, vol. III, Supplement C, pp. C9–C12 entitled "Refinement of the Modified Navy Plaque Index to Increase Plaque Scoring Efficiency in Gumline and Interproximal Tooth Areas".

*Primary Examiner*—Shep K. Rose
*Attorney, Agent, or Firm*—Henry S. Goldfine

[57] ABSTRACT

A two component efficacious dentifrice composition, having a first alkali metal bicarbonate containing dentifrice component and a second acid-containing dentifrice component; the first and second components being separated prior to use; wherein, the pH of the two components when combined upon application to the teeth is between about 6.0 and about 7.1; whereby, the dentifrice provides enhanced removal of plaque growth and a tingly mouth feel.

12 Claims, No Drawings

EFFERVESCENT TWO COMPONENT BICARBONATE AND ACID CONTAINING DENTIFRICE

BACKGROUND OF THE INVENTION

1. Field of the Invention

The present invention relates to a two component dentifrice composition, having a first component containing an alkali metal bicarbonate salt and a second component containing an acid and more particularly to such a composition which exhibits a novel tingling mouth effect and enhanced removal of plaque growth.

2. The Prior Art

The addition of alkali metal bicarbonates to toothpaste for medicinal, general cleansing, or aesthetic purposes is known in the art. These bicarbonates are used as abrasives or polishing agents in dentifrice compositions providing moderate abrasion to remove debris and stained pellicle from tooth surfaces which are accessible to the toothbrush bristles. Further, it is known that bicarbonate-acid mixtures in toothpaste formulations will create an effervescent effect and that that effervescent effect can provide certain mouth feel and moderate cleaning benefits.

British Patent 1 209 319 discloses a bicarbonate containing foaming toothpaste, based on a single composition of an alcohol-containing gel, thickened to a paste with colloidal silica and an acid salt to initiate an acid reaction. The $CO_2$ released from the acid reaction enhances the cosmetically desirable froth formation of the active detergent conventionally present in toothpaste. However, the disclosed formulation is primarily non-aqueous, having a water content of not more than 10% by weight. For such a non-aqueous dentifrice to generate any appreciable effervescence, the stabilized ingredients will have to go into solution, a relatively slow process when the neat toothpaste is first applied to the teeth. Further, the non-aqueous formulation is composed of from 20 to 50% by weight of ethanol and/or propanol, having significant taste, mouth feel and potential irritation negatives.

U.S. Pat. No. 4,487,757 discloses a dual component alkali metal bicarbonate and acid containing toothpaste, wherein the bicarbonate containing component is isolated from the acid containing component in separate sections of a multi-section storage dispenser, to avoid any chemical reaction between the bicarbonate and acid during storage. Upon dispensing the two components first contact each other and are further brought into intimate contact upon use, fostering the acid-base reaction between the bicarbonate and the acid. U.S. Pat. No. 4,487,757 discloses an effervescence which helps clean the teeth; a clean mouth or a clean "mouth feel effect"; and an initial taste which may be somewhat acidic and also salty and becomes subsequently sweeter when the acid is combined with the bicarbonate containing component, in use, in the mouth.

U.S. Pat. No. 5,474,761 discloses oral compositions effective against plaque and gingivitis, containing a nonionic water insoluble antibacterial agent, in which an essential component is bicarbonate salt. The bicarbonate is usually used at a level of from 1 to about 50 percent. Further, the pH of the disclosed oral compositions and/or the pH of such compositions in the mouth is disclosed as being safe for the mouth's hard and soft tissues, from about 8.5 to about 9.5. As will hereinafter be shown, such high pH, bicarbonate containing dentifrices will not yield any appreciable acid-base reaction and hence, will not yield any appreciable effervescence nor the desired associated attributes therewith.

U.S. Pat. No. 5,215,740 discloses a one component dentifrice composition comprising sodium bicarbonate, one or more alkali metal pyrophosphate salts, a soluble fluoride ion source and other adjuvants, in admixture with a buffering agent. The buffering agent is incorporated in the dentifrice sufficient to buffer the pH to about 8.2 to 8.9, so as to decrease the risk of irritation of the oral mucosa or desquamation, as compared with dentifrices excluding such a buffering agent. However as will hereinafter be shown, such an alkaline pH, will inhibit any significant base/acid reaction with the bicarbonate and minimize any effervescence and associated product attributes.

There is an ongoing need for new and novel mouth feel benefits to promote the use of toothpaste, especially by children, as well as, for enhanced cleaning of the oral surfaces to better remove plaque growth and hence, reduce the oral decay and disease associated with plaque.

SUMMARY OF THE INVENTION

The present invention encompasses a two component dentifrice composition, having a first alkali metal bicarbonate containing dentifrice component and a second acid-containing dentifrice component; the first and second components being separated prior to use, wherein, the pH of the two components when combined upon application to the teeth is between about 6.0 and about 7.1; whereby unexpectedly, the dentifrice provides enhanced removal of plaque growth and the user experiences a desirable tingly mouth feel.

As will hereinafter be demonstrated, at higher pH ranges, e.g. such as described in U.S. Pat. No. 5,474,761 and U.S. Pat. No. 5,215,740, bicarbonate and acid containing dentifrices do not yield any appreciable effervescence, nor any of the other attributes associated therewith.

DESCRIPTION OF THE PREFERRED EMBODIMENTS

In use, the components of the two component dentifrice of the present invention, the first containing an alkali metal bicarbonate and the second containing an acid are combined in approximately equal weight proportions, so that only about one-half of the concentration of any particular ingredient within either component will be present when the components are combined and applied to the teeth, as by brushing. Both components are formulated similarly, with the significant exception being the presence of the bicarbonate In the first component and the acid in the second component. This similarity of ingredients is to provide similar apparent physical characteristics to promote similar rheology so that the two components are delivered in the desired equal measure by extrusion from a dual compartment tube or pump device.

Dentifrice Vehicle Common to Both Components

In the preparation of the both components of the present invention, the respective acid or bicarbonate is incorporated within a pharmaceutically-acceptable dentifrice vehicle suitable for use in the oral cavity, which contains water, humectant, surfactant and a polishing agent or abrasive. The humectant is generally a mixture of humectants, such as glycerol, sorbitol and polyethylene glycol of a molecular weight in the range of 200–1000, but other mixtures of humectants and single humectants may also be employed. The humectant content within each of the two components is in the range about of 10% to about 30% by weight and preferably about 10 to about 20% by weight. The water content which is from about 30% to about 60%, and preferably from about 40 to 55% by weight.

First Component

The first toothpaste component, containing the alkali metal bicarbonate salt, is stable and non-effervescent and contains from about 5 up to, but less than, 15 percent by weight of bicarbonate. It is essential in the practice of the present invention that the pH of the toothpaste when the components are mixed in the mouth as by brushing be from about 6.0 to about 7.1. To obtain this pH in the combined toothpaste, the quantity of bicarbonate in the first component is preferably from about 8 to about 12 percent, and most preferably about 10 percent by weight whereby a pH within the first component is from about 7.5 to 9.5 and preferably from about 8.5 to 9.0. This quantity of bicarbonate salt will, in the combined toothpaste provide the desired pH and resulting effervescence, with the added benefit that the salty taste associated with bicarbonate salts is minimized.

Alkali metal bicarbonate present in the first component of the dentifrice of the present invention, includes potassium bicarbonate or sodium bicarbonate; however, sodium bicarbonate is preferred. Sodium bicarbonate is a powder composed of relatively soft particles compared to most conventional abrasive particles used in toothpastes. The size of the sodium bicarbonate particles may vary from course to fine; it is preferred that they be largely below about 0.4 mm in diameter, with a major proportion by weight being below about 0.01 mm. in diameter. Although, the vehicle in which the sodium bicarbonate particles are dispersed is an aqueous vehicle; a significant amount of the sodium bicarbonate will remain undissolved in the vehicle. However, it should be understood, that when the teeth are brushed with the combined two dentifrice components, the remaining undissolved sodium bicarbonate particles will tend to dissolve in the saliva. Such dissolving is helped by the presence of water in the toothpaste and upon such dissolution the effervescence development is speeded, and the tingly and other taste characteristics associated with the effervescence and the sodium bicarbonate are released.

Certain common toothpaste ingredients, which are basic in nature and hence not compatible with the acidic second component must, if present, be formulated in this first component of the toothpaste of the present invention. Examples of such common toothpaste ingredients include anti-tartar ingredients, such as sodium tripolyphosphate and tetrasodium pyrophosphate, and polishing agents, such as calcium carbonate and hydrated alumina.

Second Component

The second component of the toothpaste in the present invention, which is maintained physically separate from the first component prior to extrusion form the two component toothpaste tube or pump, includes within the above described pharmaceutically-acceptable dentifrice vehicle an acidic compound. Acidic compounds which can be present in the second component are malic acid, alginic acid, citric acid, succinic acid, lactic acid, tartaric acid, potassium bitartrate, acid sodium citrate, phosphoric acid, and acid phosphate and pyrophosphate salts, such as monosodium phosphate and disodium pyrophosphate. It is preferred that sodium dihydrogen phosphate, o-phosphoric acid, or sodium acid pyrophosphate be used individually or in combination. The quantity of acid compound will be from about 5 to about 15% by weight of the second component and preferably from about 8 to about 12% by weight of the second component; such that the pH of the second component is from about 1.5 to about 4.5, and preferably from about 2.5 to about 3.5; so that the pH of the combined dentifrice components upon application to the teeth is from about 6.0 to about 7.1.

Common Ingredients Within Both Components

Supplemental polishing agents or abrasives to the bicarbonate may be present in both components of the dentifrice and include sodium metaphosphate, potassium metaphosphate, tricalcium phosphate, dihydrated dicalcium phosphate, aluminum silicate, calcined alumina, or siliceous materials or combinations thereof. Preferred polishing agents include dicalcium phosphate and siliceous materials, such as silica and more preferably a precipitated amorphous hydrated silica, such as Zeodent 115, marketed by J. M. Huber Chemicals Division, Havre de Grace, Md. 21078, or Sylodent 783 marketed by Grace Davidson, Baltimore, Md. 21203.

Inorganic or organic thickeners (i.e. polymeric binders) may be included in the dentifrice of the present invention. Organic thickeners such as natural and synthetic gums and colloids may also be incorporated in the present invention. Examples of such organic thickeners include carrageenan (Irish moss), xanthan gum and sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Inorganic thickeners are preferred, include amorphous silica compounds which function as thickening agents include, colloidal silicas compounds available under tradenames such as Cab-o-sil fumed silica manufactured by Cabot Corporation and distributed by Lenape Chemical, Bound Brook, N.J., Zeodent 165 from J. M. Huber Chemicals Division, Havre de Grace, Md. 21078, and Sylox 15 from Grace Davidson, Baltimore, Md. 21203. Either inorganic or organic thickening agents, or combinations thereof, may be present in both components of the instant dentifrice in proportions of about 0.1 to about 10% by weight, preferably about 5 to about 8% in each of the two components of the instant dentifrice.

Surface active agents may be incorporated in both components of the instant invention as an ingredient to aid in the thorough dispersion of the dentifrice throughout the oral cavity when applied thereto, as well as, to improve cosmetic acceptability and the foaming properties. The surface active agents which can be included within the vehicle of both components of the instant invention include anionic, nonionic or ampholytic compounds, anionic compounds being preferred. Examples of suitable surfactants include salts of the higher alkyl sulfates, such as sodium lauryl sulfate or other suitable alkyl sulfates having 8 to 18 carbon atoms in the alkyl group; sodium lauryl sulfoacetate, salts of sulfonated monoglycerides of higher fatty acids, such as sodium coconut monoglyceride sulfonate or other suitable sulfonated monoglycerides of fatty acids of 10 to 18 carbon atoms; salts of amides of higher fatty acid, e.g., 12 to 16 carbon atom acids, with lower aliphatic amino acids, such as sodium-N-methyl-N-palmitoyl tauride, sodium N-lauroyl-, N-myristoyl- and N-palmitoyl sarcosinates; salts of the esters of such fatty acids with isotonic acid or with glycerol monosulfate, such as the sodium salt of monosulfated monoglyceride of hydrogenated coconut oil fatty acids; salts of olefin sulfonates, e.g. alkene sulfonates or alkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium, potassium or mono-, di or triethanol amine.

The surface active agent can be present in one or both components of the instant inventive compositions of the present invention at a concentration of about 0.5 to about 5.0% by weight, preferably about 1 to about 2% by weight of the particular component.

A striped dentifrice product may be obtained using the multicomponent dentifrice of the present invention, wherein colorants of contrasting colors are incorporated in each of the dentifrice components to be dispensed; the colorants being pharmacologically and physiologically non-toxic when used in the suggested amounts. Colorants used in the practice of the present invention include both pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The concentration of the dye in the dentifrice composition in an amount from about 0.0005 percent to about 2 percent by weight of the respective component.

Other ingredients which may be incorporated in one or both components of the present invention, include sweetener, flavor and preservative. The sweetener content will normally be that of an artificial or synthetic sweetener and the normal proportion thereof present will be in the range of 0.1 to 1% by weight of the respective component, preferably 0.2 to 0.5% by weight the respective component. The flavor content, which is preferably of a mixed peppermint/menthol flavor, will usually be in the range of 0.5 to 2% by weight of the respective component, preferably 0.5 to 1.0% by weight of the respective component. The contents of other components or adjuvants of the potassium salt containing dentifrice component will normally not exceed 10% by weight, often will be less than 5% by weight, and can be as low as 0%.

To prepare each of the individual dentifrice components, generally the humectants e.g. glycerin, polyethylene glycol ingredients, are mixed with any organic thickener, polymeric binder, to form a first mix. A second mix of fluoride, sweetener and water (in the case of the bicarbonate first dentifrice component, only one-half of the formulation water is added at this point) is simultaneously prepared. For the acidic second component, the acid is added into this second mix. The first and second mixes are dispersed together in a conventional mixer until the mixture therein becomes a homogeneous gel phase. Into the gel phase are added any inorganic abrasive/polishing agent or thickener, including into the first component the sodium bicarbonate which is predissolved, as much as possible, in the balance of the first component water. These ingredients are mixed until a homogeneous phase is obtained. Thereafter the flavor and surfactant ingredients are added and the ingredients mixed at high speed under vacuum of about 20–100 mm Hg. The resultant product is in each case a homogeneous, semi-solid, extrudable paste product.

The two component dentifrice composition of the present invention is packaged in a suitable dispensing container in which the components are maintained physically separated and from which the separated components may be dispensed synchronously as a ribbon for application to a toothbrush. Such containers are known in the art. An example of such a container is a two compartment dispensing container having collapsible sidewalls, as disclosed in U.S. Pat. No. 4,487, 757 and U.S. Pat. No. 4,687,663 wherein the container body is formed from a collapsible plastic web and is provided with a partition within the container body defining separate compartments in which the physically separated components are stored and from which they are dispensed through a suitable dispensing outlet.

The following examples are further illustrative of the present invention, but it are understood that the invention is not limited thereto. All amounts and proportions referred to herein and the appended claims are by weight.

EXAMPLE 1

The tooth cleaning and plaque removal efficacy of the multicomponent toothpaste of the present invention was assessed using a modified protocol based on the Rustogi Modification of the Navy Plaque index method (hereinafter Rustogi method), see Rustogi et al., *The Journal of Clinical Dentistry*, Vol. III, Supplement C, pages C9–C12 (1992). This index measures plaque removal efficacy by assessing the presence of plaque over the surface of any given tooth, both lingual and buccal, or 9 total subdivisions per side or 18 subdivisions per whole tooth, by identifing any plaque growth on the 18 subdivisions using a red plaque disclosing solution, such as D&C Red #28, marketed as Sultan Disclosing Solution Concentrate, Sultan Chemists, Inc., Englewood, N.J. 07631.

The total score for each tooth is the sum total of all sites of stained plaque on the tooth, each site either exhibiting a stain (counted as 1) or showing no stain (counted as 0). Accordingly, each tooth has a potential score of 18, if all sites show stain, indicating plaque accumulation. There is a direct correlation between the number of sites not having plaque growth and the tooth cleaning, plaque removal, efficacy of the dentifrice being tested. The lower the number having plaque or the lesser percentage of sites indicating plaque accumulation, the more effective is the antiplaque efficacy of the toothpaste.

After a week of usage, the Rustogi method was used to assess the cleaning efficacy of a two component dentifrice composition of the present invention by a panel of 5 human subjects, screened for good health and the absence of oral disease, in a cross-over, double blind (i.e. panelists and examiners are both unaware of the product being tested) panel test. The first component of the assessed dentifrice composition was an alkali metal bicarbonate containing component of the present invention, the formulation of which is presented in Table I, below. The second component of the assessed dentifrice composition was an acid containing or acidic component of the present invention, its formulation is presented in Table II, below. The combined components were designated as "Composition A."

After six days of brushing at least twice daily with Composition A, each panelist abstained from oral hygiene for a 24 hour period. After this abstention period, each of the panelists had their base-line plaque buildup assessed and scored using the Rustogi method, as discussed above. Each panelists then brushed his or her teeth using Composition A for a period of one minute and was reassessed, the plaque buildup rescored, and the reduction in sites determined to establish plaque removal efficacy. This reduction, after the one minute brushing with Composition A is recorded in Table V for each panelist.

TABLE I

Formulation Bicarbonate Component*

| Ingredients | % by Weight |
| --- | --- |
| Glycerine - USP | 18.31 |
| Polyethylene Glycol 600 | 1.00 |
| Deionized Water - Irradiated | 49.83 |
| Sodium Lauryl Sulfate | 1.50 |
| Xanthan Gum | 1.25 |
| Flavor | 0.90 |
| Sodium Fluoride | 0.49 |
| Titanium Dioxide | 0.30 |
| Tetrasodium Pyrophosphate | 0.50 |
| Sodium Saccharin | 0.30 |
| Sodium Bicarbonate | 10.00 |
| Zeodent 165 | 5.62 |
| Sylodent 783 | 10.00 |
| Total | 100.00 |

*Note: The level of each ingredient in the combination of the two component dentifrice is equal to approximately 50% of that shown within this one component.

The first bicarbonate containing component whose formulation is presented in Table I, was prepared by dispersing the formula quantities of xanthan gum and tetrasodium pyrophosphate in the glycerine and polyethylene glycol 600, using a high speed bench top mixer until a homogenous first pre-mix formed; one-half of the formula quantity of water was then used to dissolve the formula quantities of the sodium fluoride and the sodium saccharin using the high speed bench mixer to form a homogenous second premix; the balance of the water was then used to dissolve as much as possible of the sodium bicarbonate to form a third pre-mix; the first two pre-mixes were then mixed together using the high speed mixer to form a homogenous mixture and the third pre-mix was then added thereto and the mixing continued for about 15 minutes until a homogenous gel phase formed. This homogenous gel phase was transferred to a Ross type vacuum mixer and the formula quantities of the Zeodent 165 thickener and Zeodent 783 abrasive were added thereto and the mixing continued under 30 mm of Hg vacuum for 15 minutes. The formula quantities of the remaining ingredients, the sodium lauryl sulfate and flavor were then added to the Ross type vacuum mixer and this complete mixture was mixed under 30 mm of Hg vacuum for 10 minutes.

TABLE II

Formulation of Acidic Component*

| Ingredients | % by Weight |
| --- | --- |
| Glycerine - USP | 14.60 |
| Polyethylene Glycol 600 | 1.00 |
| Deionized Water - Irradiated | 50.00 |
| Sodium Lauryl Sulfate | 1.50 |
| Xanthan Gum | 1.75 |
| Flavor | 0.90 |
| Titanium Dioxide | 0.30 |
| Sodium Saccharin | 0.30 |
| Zeodent 165 | 7.65 |
| Sylodent 783 | 11.50 |
| Sodium Dihydrogen Phosphate | 5.50 |
| o-Phosphoric Acid | 3.00 |
| Sodium Acid Pyrophosphate | 2.00 |
| Total | 100.00 |

*Note: The level of each ingredient in the combination of the two component dentifrice is equal to approximately 50% of that shown within this one component.

The second acid containing or acidic component whose formulation is presented in Table II, was prepared by dispersing the formula quantities of xanthan gum in the glycerine and polyethylene glycol 600, using a high speed bench top mixer until a homogenous first pre-mix formed; one-half of the formula quantity of water was then used to dissolve the formula quantity of the titanium dioxide and the sodium saccharin using the high speed bench mixer to form a homogenous second pre-mix; the balance of the water was then used to dilute the formula quantity of o-phosphoric acid, sodium dihydrogen phosphate and sodium acid pyrophosphate to form a third pre-mix; the three pre-mixes were then mixed together using the high speed mixer to form a homogenous gel phase which was transferred to a Ross type vacuum mixer. Into this gel phase within the Ross type vacuum mixer was added the Zeodent 165 thickener and Zeodent 783 abrasive and this resulting product was mixed for 15 minutes under 30 mm of Hg vacuum. The formula quantities of the remaining ingredients, the sodium lauryl sulfate and flavor were then added to the Ross type vacuum mixer and this complete mixture was mixed under 30 mm of Hg vacuum for 20 minutes.

For purposes of comparison, the procedure of the Example I was repeated with two conventional one component dentifrice formulations, designated Control B and Control C, with the results recorded with those of Composition A in Table V. The formulations of comparative Control B and comparative Control C are shown below in Tables III and IV, respectively.

TABLE III

Comparative Control B Formulation

| Ingredients | % by Weight |
| --- | --- |
| Deionized Water-Irradiated | 7.04 |
| Polyethylene Glycol 600 | 3.00 |
| Sorbitol - 70% sol'n | 60.737 |
| Sodium Lauryl Sulfate | 1.20 |
| Sodium CMC | 0.60 |
| Flavor | 0.72 |
| Sodium Fluoride | 0.243 |
| Tetrasodium pyrophosphate | 0.50 |
| Sodium saccharin | 0.30 |
| Zeodent 115 | 25.5 |
| Blue Toothpaste Color Sol'n | 0.16 |
| Total | 100.00 |

TABLE IV

Comparative Control C Formulation

| Ingredients | % by Weight |
| --- | --- |
| Deionized Water-Irradiated | 24.94 |
| Dicalcium Phosphate Dihydrate | 48.76 |
| Glycerine-USP | 22.00 |
| Sodium Lauryl Sulfate | 1.20 |
| Sodium CMC | 1.00 |
| Flavor | 0.89 |
| Sodium Monofluorophosphate | 0.76 |
| Tetrasodium Pyrophosphate | 0.25 |
| Sodium Saccharin | 0.20 |
| Total | 100.00 |

TABLE V

Plaque Remaining

| Panelist Number | Dentifrice | Scoring Sites Tooth surfaces examined, at 18 sites per tooth | % of Sites with Plaque After 24 Hours |
|---|---|---|---|
| 1 | Composition A | 504 (28 teeth) | 44% |
| 1 | Control B | 504 | 58% |
| 1 | Control C | 504 | 60% |
| 2 | Composition A | 468 (26 teeth) | 54% |
| 2 | Control B | 468 | 74% |
| 2 | Control C | 468 | 85% |
| 3 | Composition A | 486 (27 teeth) | 49% |
| 3 | Control B | 486 | 59% |
| 3 | Control C | 486 | 65% |
| 4 | Composition A | 486 (27 teeth) | 63% |
| 4 | Control B | 486 | 70% |
| 4 | Control C | 486 | 88% |
| 5 | Composition A | 432 (24 teeth) | 49% |
| 5 | Control B | 432 | 68% |
| 5 | Control C | 432 | 50% |

The pH of Composition A, a dentifrice of the present invention, was approximated at brushing conditions in the mouth by diluting 1 part Composition A with 3 parts water to be 6.86. The pH of comparative dentrifrices Control B and Control C, were likewise ascertained at a 1:3 dilution to be 7.7 and 7.2, respectively. Referring to Table V, the plaque removal or cleaning by the two component combination of Composition A, of the present invention, was statistically different and more effective for removing plaque growth than the standard, comparative Control B (wherein p=0.02 comparing Composition A to Control B) and Control C dentifrices (wherein p<0.01 comparing Composition A to Control C).

EXAMPLE 2

The taste and mouth feel of the two component dentifrice of the present invention, Composition A, was assessed by a panel of 79 panelists using a randomized sequential monadic design test. Each panelist was given a sample of the two component dentifrice of the present invention of the formula as presented in Example I and after using it three times over the course of a day, was asked to rate the intensity level of the samples taste and sensory attributes, such as cooling, grittiness, foam, moistness, dryness, coating, tingle, salty, bitter, etc. The intensity levels were rated on a 10 level scale, from the attribute not being present at 0, to very strongly present at 10.

For purposes of comparison, the procedure of the Example 2 was repeated with a standard dentifrice of the formula of Control C, as detailed above, and with a one component, sodium bicarbonate/calcium peroxide dentifrice, Control D (having a pH of 8.65 at a 1:3 dentifrice to water dilution). The formulations of comparative Control D is presented in Table VI, below.

An analysis of the results showed that Composition A, the two component effervescent dentifrice of the present invention with a dilute "in the mouth" pH of 6.86 gave a significant tingling mouth feel. The one component, standard dentifrice of formula Control C, having a pH of 7.21, was found to give only a nominal tingling mouth feel, statistically different than the significant mouth feel provided by Composition A (within a statistically significant p=0.10). Further, the bicarbonate/peroxide dentifrice of formula Control D, with a pH of 8.65 and nominal effervescence, provided only a nominal tingling mouth feel, statistically to a significance of p=0.10, the same as the standard dentifrice of Control C and less than that of Composition A.

TABLE VI

Comparative Control D Dentifrice

| Ingredient | Weight Percent |
|---|---|
| Glycerine | 26.00 |
| Carrageenan | 0.20 |
| Sodium CMC | 0.20 |
| Polyethylene Glycol | 15.89 |
| Sodium Saccharin | 0.20 |
| Sodium monofluorophosphate | 0.76 |
| Tetrasodium pyrophosphate | 2.00 |
| Sodium Tripolyphosphate | 3.00 |
| Deionized Water | 10.00 |
| Titanium Dioxide | 0.30 |
| Zeodent 115 | 20.00 |
| Zeodent 165 | 1.50 |
| Sodium Bicarbonate | 16.00 |
| Sodium Hydroxide - 50% Solution | 1.50 |
| Calcium Peroxide | 0.50 |
| Flavor | 0.75 |
| Sodium Lauryl Sulfate | 1.20 |
| Total | 100.00 |

EXAMPLE 3

To better understand the relationship between pH and the effervescence in acid-base dentifrices, a dentifrice of the present invention was prepared using the formula of Composition A.

In a constant temperature bath, at 37° C., 10.0 grams of the bicarbonate component of Composition A (per Table I) was mixed with 10.0 grams of the acidic component of Composition A (per Table II) and 1 part of this mixture was then diluted with 3 parts water to form a slurry. The pH of this slurry was adjusted by adding 1molar HCl or 1 molar NaOH, as required, and the $CO_2$ produced was accumulated and measured. The pH was adjusted over a range of from 5.6 to 8.8 and the quantity of $CO_2$ produced from each individual slurry was measured, the results are shown in Table VII, below.

TABLE VII

Effervescence Produced at Varying pH

| pH of Dilute Dentifrice | $CO_2$ Generated (in ml) |
|---|---|
| 5.6 | 36 |
| 6.2 | 37 |
| 6.8 | 35 |
| 7.1 | 33 |
| 7.6 | 17 |
| 8.2 | 6 |
| 8.8 | 5 |

The results recorded in Table VII indicate that a pH of 7.1 or less is necessary to generate the significant $CO_2$ necessary to provide the enhanced plaque growth removal/cleaning and novel tingly mouth feel properties disclosed by the present invention. However, while pH levels less than 6.0 do generate significant $CO_2$ in dentifrices of the present invention, such lower pH imparts a negative acid taste to the dentifrice which is generally unacceptable to consumers.

What is claimed is:

1. A two component dentifrice composition comprising a first dentifrice component containing alkali metal bicarbonate in a vehicle with a humectant content of from about 10 to about 30% and a water content of about 40 to about 55% and a second dentifrice component containing acid in a vehicle with a humectant content of from about 10 to about 30% and a water content of about 40 to about 55%; the first and second dentifrice components being separated in separate compartments of a two component dentifrice dispensing means prior to use; wherein, the pH of the two dentifrice components when combined upon dispensing and application to the teeth is between about 6.0 and about 7.1; whereby, the dentifrice provides enhanced removal of plaque growth and a tingly mouth feel.

2. The composition of claim 1, wherein the alkali metal bicarbonate is sodium bicarbonate.

3. The composition of claim 1, wherein the second acid-containing dentifrice component contains either malic acid, alginic acid, citric acid, succinic acid, lactic acid, tartaric acid, potassium bitartrate, acid sodium citrate, phosphoric acid, acid phosphate or disodium pyrophosphate or combinations thereof.

4. The composition of claim 1, wherein the first alkali metal bicarbonate dentifrice component contains either sodium metaphosphate, potassium metaphosphate, tricalcium phosphate, dihydrated dicalcium phosphate, calcium carbonate, aluminum silicate, hydrated alumina, calcined alumina, or siliceous materials or combinations thereof.

5. The composition of claim 4, wherein the siliceous material is amorphous hydrated silica.

6. The composition of claim 1, wherein the first alkali metal bicarbonate component contains sodium tripolyphosphate or tetrasodium pyrophosphate or a combination thereof.

7. A method for enhancing the removal of plaque growth and providing a novel tingling mouth feel which comprises preparing a two component dentifrice; the first dentifrice component containing an alkali metal bicarbonate in a vehicle with a humectant content of from about 10 to about 30% and a water content of about 40 to about 55%, the second dentifrice component containing an acid in a vehicle with a humectant content of from about 10 to about 30° and a water content of about 40 about 55% maintaining the first and second dentifrice components separate from each other in respective compartments of a two component dentifrice dispensing means until dispensed for application to teeth; whereupon the pH of the two dentifrice components when combined to form the dentifrice composition and applied to the teeth will be between about 6.0 and 7.1.

8. The method of use of claim 7, wherein the alkali metal bicarbonate is sodium bicarbonate.

9. The method of use of claim 7, wherein the second acid-containing dentifrice component contains either malic acid, alginic acid, citric acid, succinic acid, lactic acid, tartaric acid, potassium bitartrate, acid sodium citrate, phosphoric acid, acid phosphate or disodium pyrophosphate or combinations thereof.

10. The method of use of claim 7, wherein the first alkali metal bicarbonate dentifrice component contains either sodium metaphosphate, potassium metaphosphate, tricalcium phosphate, dihydrated dicalcium phosphate, calcium carbonate, aluminum silicate, hydrated alumina, calcined alumina, or siliceous materials or combinations thereof.

11. The method of use of claim 7, wherein the siliceous material is amorphous hydrated silica.

12. The method of use of claim 7, wherein the first alkali metal bicarbonate component contains sodium tripolyphosphate or tetrasodium pyrophosphate or a combination thereof.

* * * * *